(12) United States Patent
Baumann et al.

(10) Patent No.: US 7,433,444 B2
(45) Date of Patent: Oct. 7, 2008

(54) FOCUS-DETECTOR ARRANGEMENT OF AN X-RAY APPARATUS FOR GENERATING PROJECTIVE OR TOMOGRAPHIC PHASE CONTRAST RECORDINGS

(75) Inventors: Joachim Baumann, München (DE); Christian David, Lauchringen (DE); Martin Engelhardt, München (DE); Jörg Freudenberger, Eckental (DE); Eckhard Hempel, Fürth (DE); Martin Hoheisel, Erlangen (DE); Thomas Mertelmeier, Erlangen (DE); Franz Pfeiffer, Brugg (CH); Stefan Popescu, Erlangen (DE); Manfred Schuster, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/700,060

(22) Filed: Jan. 31, 2007

(65) Prior Publication Data
US 2007/0183563 A1 Aug. 9, 2007

(30) Foreign Application Priority Data
Feb. 1, 2006 (DE) .................. 10 2006 004 604
Feb. 1, 2006 (DE) .................. 10 2006 004 976
Aug. 9, 2006 (DE) .................. 10 2006 037 255

(51) Int. Cl.
*G21K 1/00* (2006.01)
(52) U.S. Cl. .................. 378/62; 378/145; 378/146
(58) Field of Classification Search .................. 378/62, 378/145, 146, 155, 147
See application file for complete search history.

(56) References Cited
U.S. PATENT DOCUMENTS
5,812,629 A * 9/1998 Clauser .................. 378/62

2001/0001010 A1 5/2001 Wilkins
2005/0286680 A1* 12/2005 Momose .................. 378/62

FOREIGN PATENT DOCUMENTS
| DE | 10 2006 015 355.3 | 8/2007 |
| DE | 10 2006 015 356.1 | 8/2007 |
| DE | 10 2006 015 358.8 | 8/2007 |
| DE | 10 2006 017 290.6 | 8/2007 |
| DE | 10 2006 017 291.4 | 8/2007 |
| EP | 1 447 046 A1 | 8/2004 |

OTHER PUBLICATIONS

Momose, A. et al: X-ray Talbot Interferometry for Medical Phase Imaging, In: Yamada, et al: Portable Synchrotron Light sources and Advanced apllications, AIP Conference Proceedings, 2004, vol. 716, S. 156-159.
Weitkamp T. et al: X-ray phase imaging with a grating Interferometer. Optics Express, 2005, vol. 13, No. 16, S. 6296-6304.
Weitkamp et al., "X-ray phase imaging with a grating interferometer", Optics Express 2005, vol. 12, No. 16, pp. 6296-6304.

(Continued)

*Primary Examiner*—Hoon Song
(74) *Attorney, Agent, or Firm*—Harness, Dickey & Pierce P.L.C.

(57) ABSTRACT

A focus-detector arrangement of an X-ray apparatus is disclosed for generating projective or tomographic phase contrast recordings of an observed region of a subject. In at least one embodiment, the arrangement includes a radiation source which emits a coherent or quasi-coherent X-radiation and irradiates the subject, a phase grating which is arranged behind the subject in the beam path of the radiation source and generates an interference pattern of the X-radiation in a predetermined energy range, and an analysis-detector system which detects at least the interference pattern generated by the phase grating in respect of its phase shift with position resolution. Further, the beam path of the X-radiation used diverges in at least one plane between the focus and the detector.

16 Claims, 4 Drawing Sheets

OTHER PUBLICATIONS

D. Vaughan (ed.), "X-Ray Data Booklet", Lawrence Berkeley Laboratory, Berkley, 1986, pp. 2-28, 2-29.

U. Bonse and M. Hart, "An X-ray Interferometer", Appl. Phys. Lett., 1965, vol. 6, No. 8, pp. 155-156.

Ingal and Beliaevskaya, "X-ray plane-wave topography observation of the phase contrast from a non-crystalline object", J. Phys. D: Appl. Phys. 28, 1995, pp. 2314-2317.

R. Fitzgerald, "Phase-Sensitive X-Ray Interferometer", Physics Today, 53, 2000, pp. 23-26.

Chapman et al., "Diffraction enhanced x-ray imaging", Phys. Med. Biol. 42, 1997, pp. 2015-2025.

Wilkins et a., "Phase-contrast imaging using polychromatic hard X-rays", Nature 384, 1996, pp. 335-338.

V. Lehmann, The Physics of Macropore Formation in low Doped n-Type Silicon, J. Electrochemical Soc. 140 (10), 1993, pp. 2836-2843.

Bergmann, Schäfer, "Lehrbuch der Experimentalphysik", vol. 1, Mechanik, Akustik, Wärme, De Gruyter, Berlin, 1970, pp. 542-554.

Shack et al., J. Opt. Soc. Am. 61, 1971, p. 656.

Platt et al., "History and Principles of Shack-Hartmann Wavefront Sensing", Journal of Refractive Surgery, vol. 17, 2001, pp. 573-577.

F. Roddier, "Variations on a Hartmann theme", Opt. Eng. 29, 1990, pp. 1239-1242.

Primot et al., "Deconvolution from wave-front sensing: a new technique for compensating turbulence-degraded images", J. Opt. Soc. Am. 7(9), 1990, pp. 1598-1608.

J. C. Wyant, "White Light Extended Source Shearing Interferometer", Appl. Opt. 13, 1974, pp. 200-202.

C. L. Koliopoulos, "Radial grating lateral shear heterodyne interferometer", Appl. Opt. 19, 1980, pp. 1523-1528.

J. Primot, L. Songo, "Achromatic three-wave (or more) lateral shearing interferometer", J. Opt. Soc. Am. A, 12(12), 1995, pp. 2679-2685.

J. Primot, "Theoretical description of Shack-Hartmann wave-front sensor", Optics Communications, 222, 2003, pp. 81-92.

V. Ronchi, "Forty Years of History of a Grating Interferometer", Appl. Opt., 3(4), 1964, pp. 437-451.

Schroer et al., "Hard x-ray nanoprobe based on refractive x-ray lenses", Appl. Phys, Lett. 87, 124103, 2005.

M. Bavdaz, N. Gurker, "Coded Imaging X-ray Microprobe", X-Ray Spectrometry, 22, 1993, pp. 65-70.

Momose et al. "Tomographic image reconstruction using x-ray phase information", SPIE, vol. 2708, pp. 674-684.

Barty et al., "Time-gated medical imaging with ultrafast laser plasma x-rays", SPIE, vol. 2523, pp. 286-298.

C. J. Kotre, I. P. Birch, "Phase contrast enhancement of x-ray mammography: a design study", Phys. Med. Biol., 44, 1999, pp. 2853-2866.

Arfelli et al, "Low-dose phase contrast x-ray medical imaging", Phys. Med. Biol 43, 1998, pp. 2845-2852.

Herrlin et al., "Contrast-Enhanced Radiography by Differential Absorption Using a Laser-Produced X-Ray Source", Investigative Radiology 32, 1997, pp. 306-310.

Grätz et al., "Time-Gated Imaging in Radiology: Theoretical and Experimental Studies", IEEE J. of selected Topics in Quantum Electronics, 2(4), 1996, pp. 1041-1048.

Murnane et al., "Ultrafast X-ray Pulses from Laser-Produced Plasmas", Science, vol. 251, 1991, pp. 531-536.

Krol et al., "Laser-based microfocused x-ray source for mammography: Feasibiliy study", Med. Phys. 24(5), 1997, pp. 725-732.

Piestrup et al., "A design of mammography units using a quasiminichromatic x-ray source", Review of Scientific Instruments, 72(4), 2001, pp. 2159-2170.

C. G. Schroer, B. Lengler, "Focusing Hard X Rays to Nanometer Dimensions by Adiabatically Focusing Lenses", Phys. Rev. Lett. 94, 054802, 2005.

* cited by examiner

FOCUS-DETECTOR ARRANGEMENT OF AN X-RAY APPARATUS FOR GENERATING PROJECTIVE OR TOMOGRAPHIC PHASE CONTRAST RECORDINGS

PRIORITY STATEMENT

The present application hereby claims priority under 35 U.S.C. §119 on German patent application numbers DE 10 2006 004 976.4 filed Feb. 1, 2006, DE 10 2006 004 604.8 filed Feb. 1, 2006, and DE 10 2006 037 255.7 filed Aug. 9, 2006, the entire contents of each of which is hereby incorporated herein by reference.

FIELD

Embodiments of the invention generally relate to a focus-detector arrangement of an X-ray apparatus for generating projective or tomographic phase contrast recordings of an observed region (=FOV=Field of View) of a subject. For example, an embodiment may relate to one having a radiation source which emits coherent or quasi-coherent X-radiation and irradiates the subject, a phase grating which is arranged behind the subject in the beam path of the radiation source and generates an interference pattern of the X-radiation in a pre-determined energy range, and an analysis-detector system which detects at least the interference pattern generated by the phase grating in respect of its phase shift with position resolution.

BACKGROUND

For X-ray imaging, two effects which occur when X-rays pass through matter are usually considered, namely the absorption of a particular component of the X-rays and the phase shift of the transmitted X-rays.

In respect of the refractive index, which is given for X-rays by $$n = 1 - \delta - i\beta, \quad (1)$$

the absorption depends on the size of the imaginary decrement $\beta$, which is related to the mass absorption coefficient $\mu/\rho$ by $$\mu/\rho = 4\pi\beta/\lambda, \quad (2)$$

where $\lambda$ is the wavelength, $\mu$ is the linear absorption coefficient and $\rho$ is the mass density.

The phase shift follows from the real part of the refractive index $1-\delta$. The phase shift $\Delta$ of an X-ray wave in matter compared to a vacuum is given by $$\Delta = 2\pi\delta T/\lambda, \quad (3)$$

where $T$ is the thickness of the material and $\delta$ is the real decrement of the refractive index.

In X-radiography, the subject is exposed to X-rays and the transmitted intensity is recorded behind the object. With the aid of this measurement, projection images can be produced which show the absorption caused by the object. In X-ray tomography, more than one projection image is used in order to calculate a three-dimensional data set, which shows the spatial distribution of the absorption coefficients $\mu$.

For phase contrast radiography and phase contrast tomography, it is necessary to evaluate the phase shift caused by the object. Similarly as absorption imaging, a three-dimensional data set can be calculated which shows the spatial distribution of the real part of the refractive index $1-\delta$.

Since the phase of a wave cannot be measured directly, the phase shift is firstly converted into a measurable intensity by interference of the wave to be studied with a reference wave. The practical conduct of such measurements, both in relation to projective recordings and in relation to tomographic recordings, is presented by way of example in the European patent application EP 1 447 046 A1 and in the German patent applications with the file references 10 2006 017 290.6, 10 2006 015 358.8, 10 2006 017 291.4, 10 2006 015 356.1 and 10 2006 015 355.3 of the same priority.

The method presented there uses a phase grating placed in the beam path behind the subject, which acts as a diffraction grating and splits the X-rays into $+1^{st}$ and $-1^{st}$ order rays. In the wave field behind the phase grating, the diffracted rays interfere with one another to form an X-ray standing wave field. The subject causes local phase shifts, which deform the wavefront and therefore locally modify the amplitude, phase and offset of the standing wave field. By using a measurement which delivers information about the standing wave field, such as the phase, amplitude and average value of the standing waves, it is therefore possible to calculate the influence of the local phase shifts due to the subject. In order to scan the wave field with the requisite resolution, an analyzer grating is displaced stepwise over the wave field while the intensity is synchronously monitored pixel-wise by using a corresponding detector.

In the European patent application EP 1 447 046 A1 cited above, parallel X-rays are used for scanning the subject. Considered superficially, it could be assumed that an arbitrary magnification effect would be achievable by using divergent radiation geometries and correspondingly positioning the subject in the beam path. But when considering the effect of the radiation being refracted by the subject, it is found that measurement of the phase shift no longer appears possible because it is to be expected that a "chaotic" pattern of the deviated rays will occur, which does not lead to an evaluatable image rendition. For this reason, no X-ray phase contrast measurements have actually been carried out in a magnifying geometry by using phase gratings.

SUMMARY

In at least one embodiment of the invention, a focus-detector arrangement is provided for X-ray phase contrast radiography and X-ray phase contrast tomography, which makes it possible to generate magnifying to highly magnifying projective and tomographic representations of the spatial distribution of the refractive index of a subject.

In respect of X-ray phase contrast measurement with the aid of phase gratings and coherent or quasi-coherent X-radiation, the following should also essentially be pointed out:

The emission of X-ray photons from laboratory X-ray sources (X-ray tubes, secondary targets, plasma sources, parametric X-ray sources, channeling radiation) as well as by conventional synchrotron radiation sources of the first to third generations is subject to stochastic processes. The emitted X-radiation therefore has no spatial coherence per se. In phase contrast radiography and tomography or any interference experiment, however, the radiation of X-ray sources behaves as coherent radiation when the observation angle at which the source appears to the observer or the object, the grating or the detector, is sufficiently small. The so-called spatial/transverse (lateral) coherence length $L_c$ can be provided as a measure of the spatial or transverse coherence of an extended X-ray source:

$$L_c = \lambda \frac{a}{s}. \tag{4}$$

Here, $\lambda$ is the wavelength, s is the transverse source size and a is the source-observation point distance. The exact value is incidental; what is important is that the coherence length L is large compared to the (lateral) dimension of the spatial region from which rays are intended to interfere with one another.

In the context of the patent application, the term coherent radiation is intended to mean radiation which leads to the formation of an interference pattern under given geometries and given distances of the X-ray optical gratings. It is self-evident that the spatial coherence and therefore the spatial coherence length is always determined by the trio of quantities: wavelength, source size and observation distance. With a view to compact formulation, this fact has been abbreviated to terms such as "coherent X-radiation", "coherent X-radiation source" or "point source for generating coherent X-radiation". The basis for these abbreviations is that the wavelength (or the energy E) of the X-radiation in the applications discussed here is limited by the desired penetrability of the subject on the one hand and the spectrum available in laboratory X-ray sources on the other hand. The distance a between the source and the observation point is also subject to certain restrictions in laboratory equipment for nondestructive material testing or medical diagnosis. This usually leaves only the source size s as a single degree of freedom, even though the relationships between source size and tube power likewise set narrow limits here.

Higher-power radiation sources and therefore larger focus dimensions can be used in the focus-detector arrangement in question here if a suitably dimensioned source grating is used. The narrow slits of the source grating ensure that all the rays, which have to emerge from the same slit, comply with the requisite spatial coherence. Photons from the same slit can interfere with one another, i.e. be superposed with correct phase. Between the photons from different slits of the source grating, however, no correctly phased superposition is possible. Yet with suitable tuning of the source grating period $g_0$ and the interference pattern period $g_2$ as well as the spacing l of the source grating $G_0$ and the phase grating $G_1$, and the spacing d of the phase grating $G_1$, and the interference pattern $G_2$, to first approximation according to $$g_0/g_2 = l/d, \tag{5}$$

correct superposition of the wave maxima and the wave minima of the standing wave field is possible at least in respect of intensity. In the abbreviated formulation of the patent application, the term "quasi-coherent radiation" or "quasi-coherent radiation source" is used in this context.

The temporal or longitudinal coherence of the radiation is associated with the monochromaticity of the X-radiation or of the X-radiation source. The X-radiation of intense characteristic lines usually has a sufficient monochromaticity or temporal coherence length for the applications discussed here. Upstream monochromators or selection of the resonant energy via the bar height of the phase grating can also filter out a sufficiently narrow spectral range from a Bremsstrahlung spectrum or synchrotron spectrum, and thus satisfy the requirements for the temporal coherence length in the present arrangements.

Contrary to the conventional wisdom that a magnifying structure of a focus-detector arrangement for phase contrast measurement is not possible, the Inventors have found that satisfactory image results can be achieved against all expectations.

According to this discovery, in at least one embodiment, the Inventors provide a focus-detector arrangement of an X-ray apparatus for generating projective or tomographic phase contrast recordings of an observed region (=FOV=Field of View) of a subject, which comprises:

a radiation source which emits a coherent or quasi-coherent X-radiation and irradiates the subject, a phase grating which is arranged behind the subject in the beam path of the radiation source and generates an interference pattern of the X-radiation in a predetermined energy range, and an analysis-detector system which detects at least the interference pattern generated by the phase grating in respect of its phase shift with position resolution, wherein the beam path of the X-radiation used diverges in at least one plane between the focus and the detector, i.e. corresponds to a fan beam.

In another embodiment, the focus-detector arrangement may also be configured so that the beam path of the X-radiation used diverges two planes between the focus and the detector, and therefore corresponds to a cone beam.

For a compact structure, it is particularly advantageous for there to be a divergence of the ray beam used of at least 5°, preferably at least 10° in at least one plane. For an application in the field of medical computer tomography, fan angles of more than 45° are even used.

According to the divergence of the beam geometry used, the observed region of the subject—as seen in projection in the direction of the optical axis of the beam path—may be dimensioned smaller than the utilized region of the phase grating) downstream in the beam path, which in turn may be dimensioned smaller than the utilized region of the analysis-detector system downstream in the beam path. Of course, this also applies correspondingly with a reverse observation mode starting from the focus with increasing dimensioning.

According to an example embodiment, the distance from the radiation source to the analysis-detector system is at least two times as great as the distance from the radiation source to the subject. This, by using a phase grating and the described analysis-detector system, for the first time allows an effectively magnifying phase contrast recording in which only the phase shift is represented in the image. With relevant requirements, this magnification factor may be extended to up to 10 times or even 1000 times magnification via an appropriate selection of distance between the X-ray source and the subject and between the X-ray source and the analysis-detector system.

In the focus-detector arrangement, it is proposed that the following geometrical relationship be satisfied in respect of the periods of the phase grating and analysis grating:

$$g_2 = \frac{1}{2} \frac{r_1 + d_m}{r_1} g_1, \tag{6}$$

where $d_m$ corresponds to the distance between the gratings, $r_1$ corresponds to the distance between the radiation source and the first grating, $g_2$ corresponds to the period of the analyzer grating, and $g_1$ corresponds to the period of the phase grating.

With the relationship $r_2=r_1+d_m$, Equation (6) can also be rewritten as $$g_2 = \frac{1}{2}\frac{r_2}{r_1}g_1.$$

It is furthermore proposed to position the analysis-detector system so that the analyzer grating, when the analysis-detector system includes a detector with an analyzer grating, or the entry side of the detector when the analysis-grating system includes a detector without an analyzer grating, is at a distance from the phase grating such that the standing wave field is maximally pronounced. The following applies to first approximation for this so-called Talbot distance:

$$d_m = \left(m - \frac{1}{2}\right) \cdot \frac{g_1^2}{4 \cdot \lambda}, \quad (7)$$

where:
$d_m$=distance from the phase grating to the analyzer grating, so-called Talbot distance;
m=order of the Talbot-interference; m=1, 2, 3, . . . ;
$g_1$=period of the phase grating;
$\lambda$=wavelength of the X-radiation used.

Formula (7) describes the exact distance for a parallel beam. When using a cone beam, Formula (7) applies only to first approximation since the interference pattern spreads more and more with an increasing distance from the phase grating, as described in Formula (6). This corresponds in practice to a grating period $g_1$ of the phase grating which becomes ever larger with an increasing distance.

According to at least one embodiment of the invention, two different variants of the relative arrangement of the phase grating and the analysis-detector system can be set up in this embodiment of a focus-detector arrangement. If the phase grating is arranged closer to the analysis-detector system than to the subject in the radiation direction, then the grating period of the amplitude grating in the analysis-detector system will be smaller than the grating period of the phase grating, typically about half as large.

In the alternative focus-detector arrangement in which the phase grating is arranged closer to the subject than to the detector in the radiation direction, it is possible to work with larger grating periods of the analyzer grating. It is even possible to work with a grating period of the analyzer grating which is greater than that of the phase grating.

Both variants mentioned last may also be configured with an analysis-detector system which, instead of an analyzer grating, comprises a detector whose individual detector elements are furthermore designed to be strip-shaped with alignment according to the grating lines of the phase grating, in which case the strips must have a period of at most ⅓ of the corresponding period of an analyzer grating in order to be able to determine the phase shift of the X-ray in the detector element with a single measurement.

In order to generate the coherent X-radiation, in a first alternative embodiment, the Inventors propose that the radiation source should have a focus which is designed as a microfocus in relation to the geometrical proportions of the focus-detector arrangement.

According to another alternative embodiment, the radiation source may include an extended focus if an X-ray optical grating arranged in the beam direction, a so-called source grating, additionally ensures the required coherence. Although this entails a restriction in respect of the possible achievable resolution, the power can nevertheless be increased so that, for example, the required exposure times can be reduced.

Although the variants mentioned above are example embodiments of the invention, all other known X-ray sources which generate coherent X-ray light—for example so-called free electron lasers, $4^{th}$ generation synchrotrons—likewise fall within the scope of the invention, a divergent beam geometry respectively being a prerequisite.

According to the discovery by the Inventors, they also propose that the focus-detector arrangement according to at least one embodiment of the invention be used in conjunction with an X-ray system for generating projective phase contrast recordings or in conjunction with an X-ray computer tomography system for generating tomographic phase contrast recordings, in each case with a magnifying representation of a subject. Such systems are usually employed in connection with the analysis of small samples, but also for detailed imaging in medical computer tomography or examination of small animals.

BRIEF DESCRIPTION OF THE DRAWINGS

The invention will be explained in more detail below with reference to example embodiments with the aid of the figures, only the features necessary for understanding the invention being represented. Here, the following references are used: 1: computer tomography system; 2: first X-ray tube; 3: first detector; 4: second X-ray tube; 5: second detector; 6: gantry housing; 7: patient; 8: patient support; 9: system axis; 10: control and computation unit; 11: memory; d: distance from the phase grating $G_1$ to the analyzer grating $G_2$; D: detector; $d_m$: Talbot distance; $E_i$, $E_j$: detector elements; F: focus; $G_0$: source grating; $G_1$: phase grating; $G_2$: analyzer grating; $g_1$, $g_2$: grating period; $I(E_x(x_G))$: measured intensity at the detector elements $E_x$, with the grating offset $x_G$; I: measured intensity of the photon flux; M: interference pattern; P: sample; $Prg_n$: program; $\overline{QD}$: distance from source to analyzer-detector system; $\overline{QP}$: distance from source to sample; $r_1$: radial distance from the focus to the phase grating; $r_2$: radial distance from the focus to the analyzer-detector system; $S_i$: X-rays; $x_G$: offset of the analyzer grating; $\phi$: phase shift at the detector element $E_x$; $\phi_{ij}$: relative phase shift between the detector elements; $\lambda$: wavelength of the energy of the X-radiation used.

In detail.

DETAILED DESCRIPTION OF THE EXAMPLE EMBODIMENTS

Figure 1:
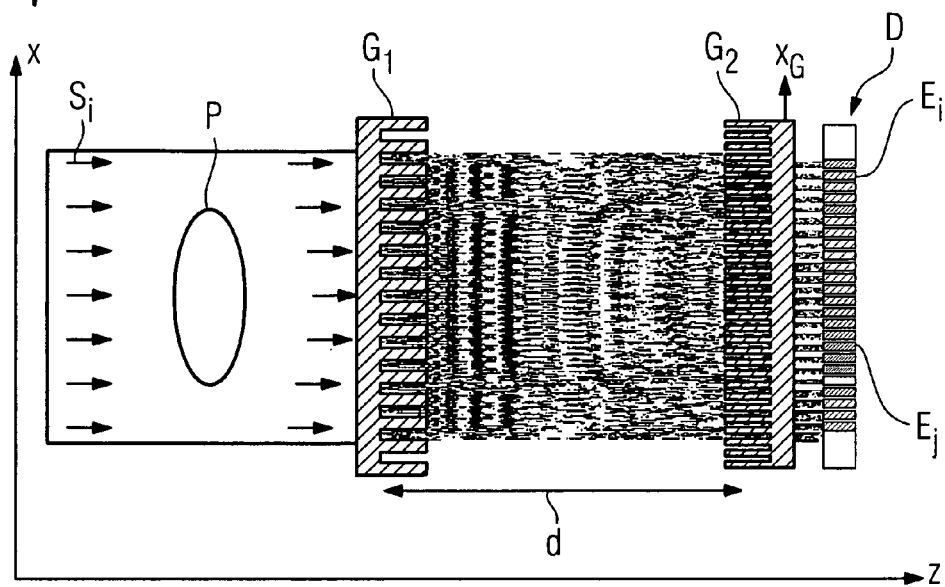
FIG. 1: shows a longitudinal section through an outline representation of a focus-detector arrangement with a phase grating, analyzer grating and detector for representing the interference phenomenon.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

For better understanding, the basic principle of phase contrast measurement will be described below with FIGS. 1 to 2.

FIG. 1 shows coherent radiation coming from a point-like radiation source or individually quasi-coherent radiation coming from a source grating, which passes through a subject or sample P, a phase shift taking place when passing through the subject P. When passing through the grating $G_1$ an interference pattern is generated, as represented by the gray shading, which with the aid of the grating $G_2$ leads to different radiation intensities per detector element on the downstream detector D and its detector elements $E_i$, $E_j$, an interference pattern or X-ray standing wave field being formed at a so-called Talbot distance.

Figure 2:
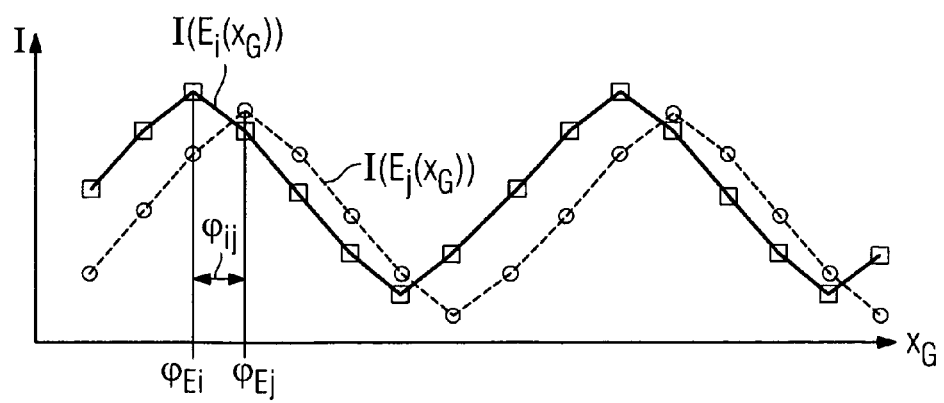
FIG. 2: shows the intensity profile on selected detector elements as a function of the relative position of the analyzer grating with respect to the interference pattern.

If the detector element $E_i$ for example is considered as a function of the relative position $x_G$ of the analyzer grating $G_2$ and the intensity $I(E_i(x_G))$ is plotted as a function of the relative position $x_G$, then a sinusoidal profile of the intensity I at this detector element $E_i$ is obtained as shown in FIG. 2. If this measured radiation intensity I is plotted for each detector element $E_i$ or $E_j$ as a function of the offset $x_G$, then the function $I(E_i(x_G))$ or $I(E_j(x_G))$ can be approximated for the various detector elements, which in the end form the geometrical X-ray between the focus and the respective detector element. The phase shift $\phi$ and the relative phase shift $\phi_{ij}$ between the detector elements can be determined for each detector element from the functions.

For each ray in space, the phase shift per detector pixel or ray considered can therefore be determined by at least three measurements with a respectively offset analyzer grating, from which either the pixel values of a projective recording can be calculated directly in the case of projective X-ray recordings. On the other hand, projections whose pixel values correspond to the phase shift are compiled in the case of a CT examination, so that with the aid of reconstruction methods known per se it is possible to calculate therefrom which volume element in the subject is to be ascribed to which component of the measured phase shift. Section images or volume data are thus calculated therefrom, which reflect the effect of the examined object in respect of the phase shift of X-radiation with position resolution. Since even minor differences exert a strong effect on the phase shift in this context, very detailed and high-contrast volume data can be obtained from materials which are relatively similar per se, in particular soft tissue.

This variant of detecting phase shifts of the X-rays which pass through a subject, with the aid of a multiply offset analyzer grating and measuring the radiation intensity on a detector element behind the analyzer grating, means that at least three measurements of each X-ray have to be carried out with an analyzer grating respectively displaced by fractions of the grating period.

In principle, it is even possible to make do without such an analyzer grating and use a sufficiently fine-structured detector instead, in which case the intensity losses due to absorption in the bars of the analyzer grating are obviated and the phase shift between the individual rays/pixels can be determined by a single measurement.

In order to measure the phase contrast, it is necessary to use coherent or at least quasi-coherent radiation. This may be generated for example by a point-like focus or as a field of quasi-coherent radiation by a source grating behind a focus, which is designed to be flat, or by a corresponding grating-like configuration of the focal spot on the anode in order to replicate such a grating.

The line orientation of the gratings should be selected so that the grating lines of the gratings provided, and the possibly provided strip structures of the detector elements, extend mutually parallel. It is furthermore advantageous, but not necessary, that the grating lines should be oriented parallel or perpendicularly to the system axis of the focus-detector system presented here.

Figure 3:
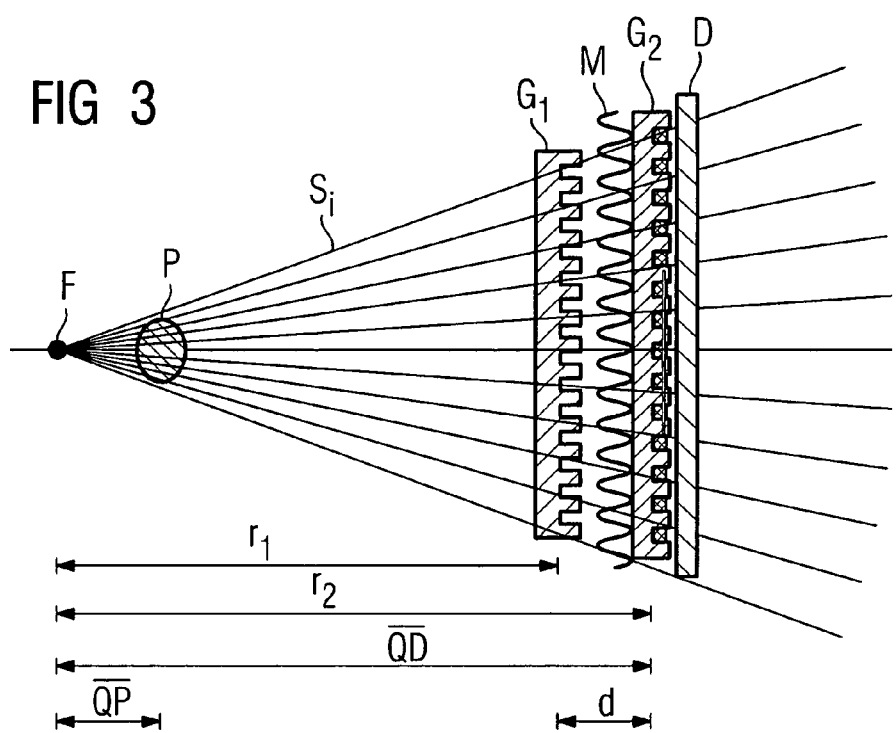
FIG. 3: shows a schematic sectional representation of a focus-detector combination according to an embodiment of the invention with a strong magnification effect and a phase grating in the vicinity of the analyzer-detector system.

FIG. 3 shows a schematic representation of a focus-detector combination according to an embodiment of the invention having a focus F, which emits a divergent ray beam with the rays $S_i$ in the direction of a sample or subject P. After passing through the subject P the ray bundle, now broadened, strikes a first phase grating $G_1$ in which an interference pattern is generated, which is evaluated by the downstream analysis-detector system with the analyzer grating $G_2$ and the subsequent detector D. The evaluation by such an evaluation-detector system as presented here, having an analyzer grating and a downstream detector with a multiplicity of detector elements, takes place as was described in FIGS. 1 and 2. In order to improve the effectiveness of the analyzer grating $G_2$, a highly absorbent material is additionally represented in the grating gaps of the grating $G_2$. It will however be pointed out that analyzer gratings without such a filler in the grating gaps also belong to the scope of the invention.

The relevant radial distances between the essential elements of the focus-detector combination are moreover represented below the figure, such as the radial distance $r_1$, between the focus and the phase grating $G_1$ and the radial distance $r_2$ between the focus and the analysis-detector system. In order to describe the magnifying properties of the divergent rays, the distances between the focus or source and the sample $\overline{QP}$ and the distance between the source or focus and the analysis-detector system $\overline{QD}$ are likewise indicated. The magnification factor V is given by the distance ratio between the distance $\overline{QD}$ from the source or focus to the analysis-detector system and the distance $\overline{QP}$ from the source or focus to the sample, with $$V = \frac{\overline{QD}}{\overline{QP}}. \tag{8}$$

The size of the projections of the scanned region in the subject (=FOV=Field of View) with respect to the utilized region of the subsequent phase grating $G_1$ as well as to the utilized subsequent region of the analyzer-detector system also behave according to this geometrical situation in an embodiment of the inventive scanning of a subject.

Figure 4:
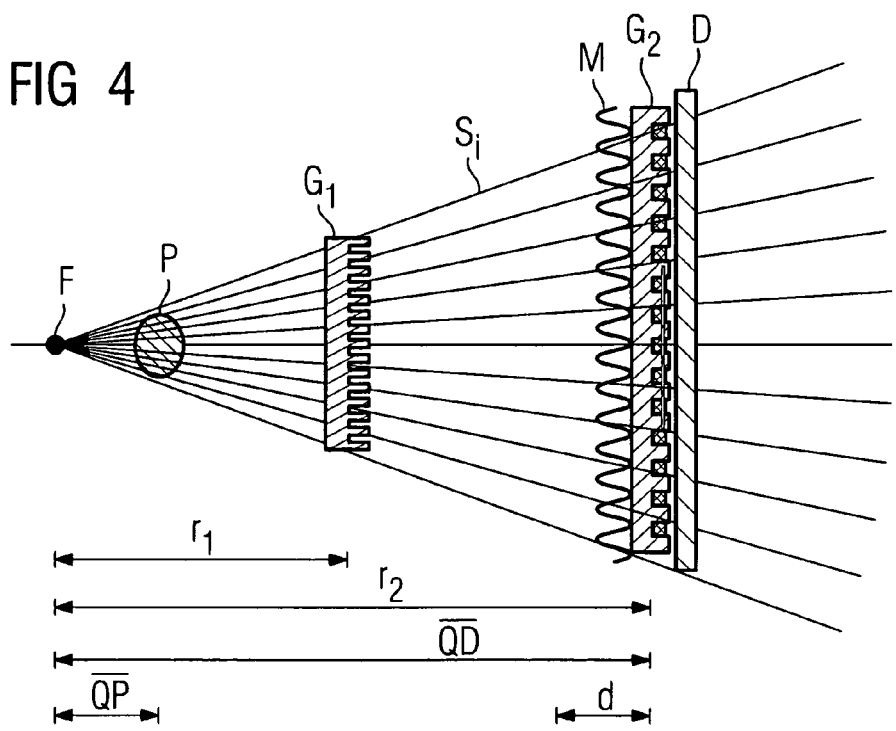
FIG. 4: shows a schematic sectional representation of a focus-detector combination according to an embodiment of the invention with a strong magnification effect and a phase grating in the vicinity of the subject.

FIG. 4 represents a variant of a focus-detector system likewise according to an embodiment of the invention, in which the distance between the phase grating and the subsequent analysis-detector system is substantially increased. The Inventors have discovered that a larger Talbot distance can be achieved by selecting a higher Talbot order m and/or by increasing the phase grating period $g_1$. Enlarging $g_1$, moreover, also entails a larger period of the analyzer grating. Above all, however, the period of the standing wave field to be scanned and therefore also the period of the analyzer grating are increased by the geometrical enlargement. This reduces the aspect ratio and therefore facilitates production of the gratings. If the analysis-detector system is to be configured without an analyzer grating, then the spatial resolution requirements of the detector can advantageously be selected to be less stringent via the geometry as described above.

Figure 5:
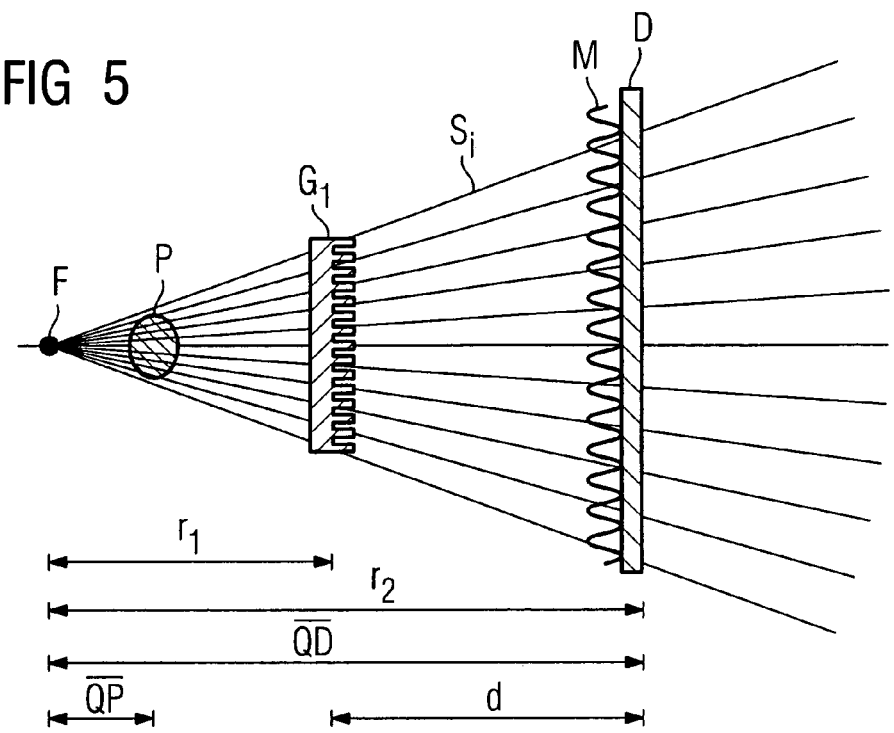
FIG. 5: shows a schematic sectional representation of a focus-detector combination according to an embodiment of the invention with a strong magnification effect and the use of an analyzer-detector system without an analyzer grating.

Such a variant of a focus-detector system having a phase grating $G_1$ for interference formation with a downstream analysis-detector system, in which the detector is divided into individual detector elements and these detector elements, which determine the position resolution of the detector, are furthermore subdivided into strip shapes according to the grating lines of the phase grating in order to measure the phase shift per detector element, is represented in FIG. 5. Here again, the distance between the phase grating $G_1$ and the subsequent detector D is selected to be so large that it corresponds to the Talbot distance $d_m$.

Figure 6:
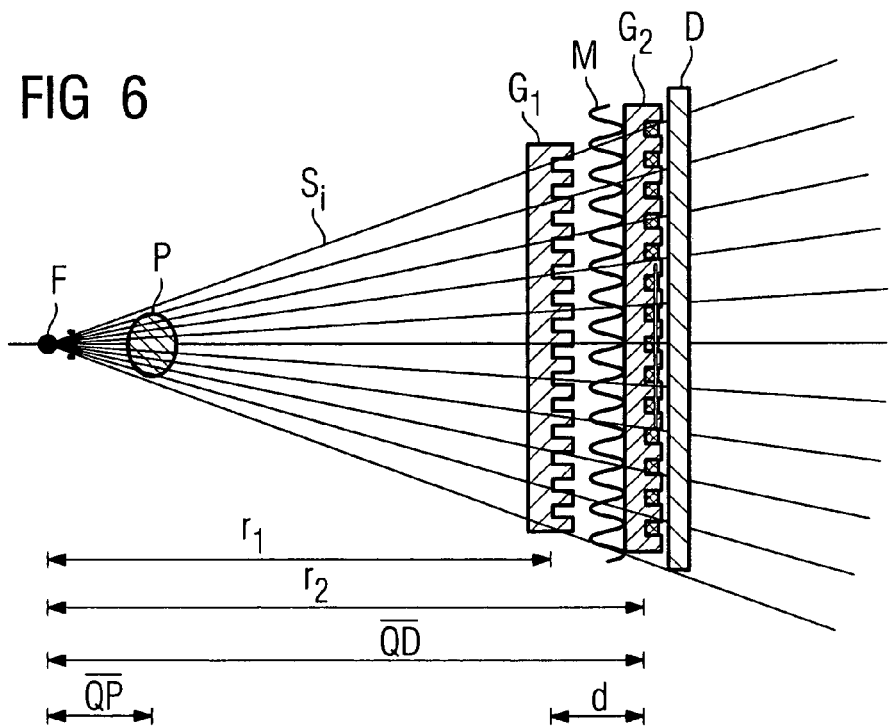
FIG. 6: shows a schematic sectional representation of a focus-detector combination according to an embodiment of the invention with a strong magnification effect and a phase grating in the vicinity of the analyzer-detector system, with the use of a source grating at the radiation source.
Figure 7:
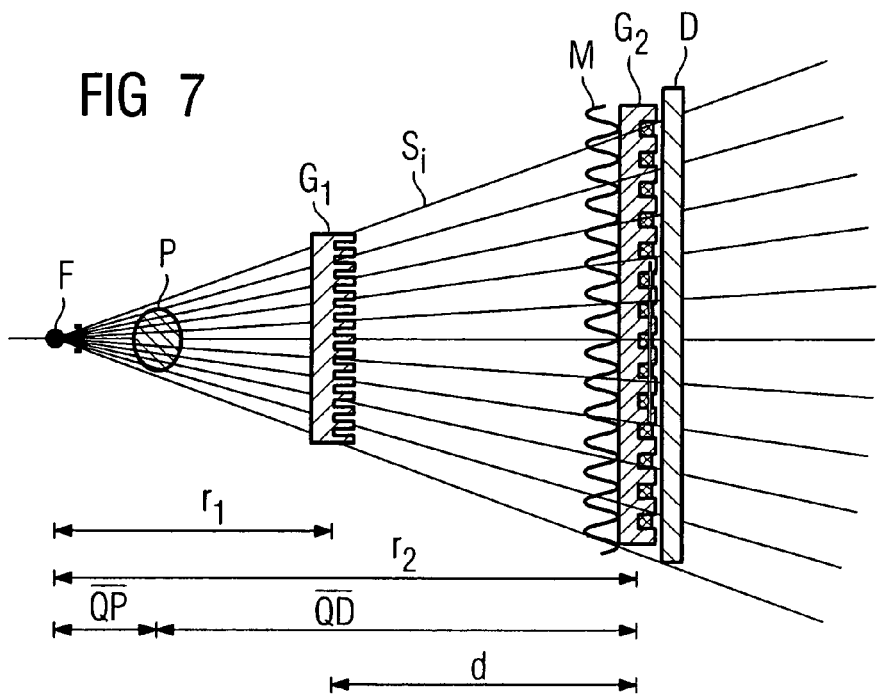
FIG. 7: shows a schematic sectional representation of a focus-detector combination according to an embodiment of the invention with a strong magnification effect and a phase grating in the vicinity of the subject, with the use of a source grating at the radiation source.

FIGS. 6 and 7 represent a variant of a focus-detector system in which an additional source grating is interposed between the focus F and the subject P, so that quasi-coherent X-radiation can be generated even with an extended focus and it is therefore possible to work with a substantially higher power/intensity.

This provides the opportunity to use such focus-detector systems also in conjunction with medically used projective X-ray equipment or computer tomographic systems.

The mutual distance ratios of the gratings in FIGS. 6 and 7 correspond to the distance ratios of FIGS. 3 and 4.

Figure 8:
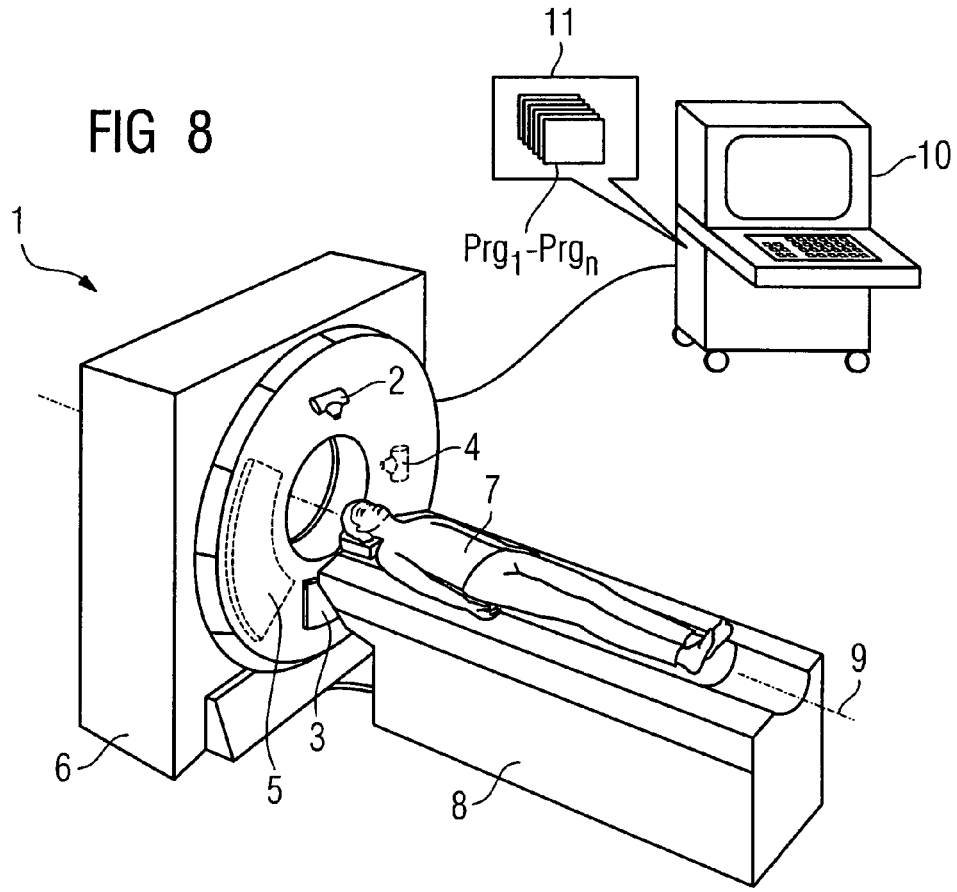
FIG. 8: shows a schematic representation of a computer tomography system having a focus-detector combination according to an embodiment. of the invention with a magnification effect and a phase grating, with the use of a source grating at the radiation source.

FIG. 8 represents a computer tomography system 1 by way of example of a medical application, which comprises one or optionally two focus-detector systems. A gantry housing 6 is represented, which contains a first X-ray tube 2 with a detector system 3 lying opposite, in which a phase grating as represented in the drawings described above is also integrated. Optionally, a further focus-detector system with a second X-ray tube 4 and a second detector system 5 may additionally be provided. As the subject, a patient 7 may be displaced through the opening in the gantry for the purpose of a scan along the system axis 9 with the aid of a displaceable patient table 8. The computer tomography system is controlled and evaluated with the aid of a computation and control unit 10, in which there is a memory which contains Programs $Prg_1$, to $Prg_n$. The evaluation of the recordings and their reconstruction may also be carried out in this control and computation unit 10.

It should also be pointed out that the focus-detector systems presented here in the document are not only capable of carrying out phase contrast measurements, rather absorption measurements may also be carried out. Phase and absorption information is obtained when evaluating each individual pixel.

It is to be understood that the features of the invention as mentioned above may be used not only in the combination respectively indicated, but also in other combinations or in isolation, without departing from the scope of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A focus-detector arrangement of an X-ray apparatus for generating at least one of projective and tomographic phase contrast recordings of an observed region of a subject, comprising:

a radiation source to emit at least one of a coherent and quasi-coherent X-radiation and to irradiate the subject;

a phase grating, arranged behind the subject in a direction of a beam path from the radiation source, to generate an interference pattern of the X-radiation in an energy range; and an analysis-detector system including an analyzer grating, to detect at least the interference pattern generated by the phase grating in respect of its phase shift with position resolution, wherein the beam path of the X-radiation used diverges in at least one plane between the focus and the detector, wherein the following geometrical relationship is satisfied:

$$g_2 = \frac{1}{2} \frac{r_1 + d}{r_1} g_1,$$

where d corresponds to the distance between the phase grating $G_1$ and the analyzer grating $G_2$, $r_1$ corresponds to the distance between the radiation source and the phase grating, $g_2$ corresponds to the period of the analyzer grating ($G_2$), and $g_1$ corresponds to the period of the phase grating ($G_1$).

2. The focus-detector arrangement as claimed in claim 1, wherein the beam path of the X-radiation used diverges in two planes between the focus and the detector.

3. The focus-detector arrangement as claimed in claim 1, wherein the region of the subject, as seen in projection in the direction of the optical axis of the beam path, is relatively smaller than the utilized region of the phase grating downstream in the beam path, which in turn is relatively smaller than the utilized region of the analysis-detector system downstream in the beam path.

4. The focus-detector arrangement as claimed in claim 1, wherein the distance from the radiation source to the analysis-detector system is at least two times as great as the distance from the radiation source to the subject.

5. The focus-detector arrangement as claimed in claim 1, wherein the distance from the radiation source to the detector of the analysis-detector system is at least 10× as great as the distance from the radiation source to the subject.

6. The focus-detector arrangement as claimed in claim 1, wherein the phase grating is arranged relatively closer to the analysis-detector system than to the subject in the beam direction.

7. The focus-detector arrangement as claimed in claim 1, wherein the phase grating is arranged relatively closer to the subject than to the analysis-detector system in the beam direction.

8. The focus-detector arrangement as claimed in claim 1, wherein the analysis-detector system comprises an analyzer grating with a detector downstream in the beam direction having a multiplicity of detector elements.

9. The focus-detector arrangement as claimed in claim 8, wherein the distance ($d_m$) from the phase grating ($G_1$) to the analyzer grating ($G_2$) fulfills the following geometrical relationship:

$$d_m = \left(m - \frac{1}{2}\right) \cdot \frac{g_1^2}{4 \cdot \lambda},$$

where:
$d_m$=distance from the phase grating ($G_1$) to the analyzer grating ($G_2$);
m=1,2,3,...;
$g_1$=grating period of the phase grating ($G_1$);
$\lambda$=wavelength of the X-radiation used.

10. The focus-detector arrangement as claimed in claim 1, wherein the radiation source comprises a focus which is designed as a microfocus in relation to the geometrical proportions of the focus-detector arrangement, such that:

$$s \leq \lambda \frac{r_1}{g_1}$$

with the size s of the focus, the wavelength $\lambda$ of the radiation used, the radial distance $r_1$ from the focus to the phase grating and the grating period $g_1$ of the phase grating.

11. The focus-detector arrangement as claimed in claim 1, wherein the radiation source comprises a focus and an X-ray optical grating arranged in the beam direction.

12. An X-ray system for generating projective phase contrast recordings with a magnified representation of a subject, comprising the focus-detector arrangement as claimed in claim 1.

13. An X-ray computer tomography system for generating tomographic phase contrast recordings with a magnifying representation of a subject, comprising the focus-detector arrangement as claimed in claim 1.

14. The focus-detector arrangement as claimed in claim 2, wherein the region of the subject, as seen in projection in the direction of the optical axis of the beam path, is relatively smaller than the utilized region of the phase grating downstream in the beam path, which in turn is relatively smaller than the utilized region of the analysis-detector system downstream in the beam path.

15. The focus-detector arrangement as claimed in claim 1, wherein the phase grating is arranged between the subject and the analysis-detector system.

16. The focus-detector arrangement as claimed in claim 1, wherein the analysis-detector system measures a quantitative phase displacement of each ray of the emitted radiation using at least three measuring operations.

* * * * *